United States Patent [19]
Passafaro et al.

[11] Patent Number: 6,139,557
[45] Date of Patent: Oct. 31, 2000

[54] APPARATUS FOR MAKING WIRE WITH RADIAL EXPANSIBLE GUIDE SECTION AND METHODS OF MANUFACTURING THE SAME

[75] Inventors: James D. Passafaro, Los Gatos; Larry B. Rogers, Half Moon Bay; Kathy M. Mah, Mountain View; Roger W. Perkins; Joan Huynh, both of San Jose, all of Calif.

[73] Assignee: Prolifix Medical, Inc., Sunnyvale, Calif.

[21] Appl. No.: 09/290,510

[22] Filed: Apr. 12, 1999

Related U.S. Application Data

[63] Continuation-in-part of application No. 08/966,001, Nov. 7, 1997.
[60] Provisional application No. 60/081,631, Apr. 13, 1998, provisional application No. 60/103,447, Oct. 7, 1998, and provisional application No. 60/081,614, Apr. 13, 1998.

[51] Int. Cl.[7] ................................................. A61B 17/32
[52] U.S. Cl. .............................................. 606/159; 600/585
[58] Field of Search ................................. 606/159, 170, 606/180; 600/585, 434, 435; 128/772; 604/95, 280–285; 72/135, 146

[56] References Cited

U.S. PATENT DOCUMENTS

| | | |
|---|---|---|
| 4,706,671 | 11/1987 | Weinrib . |
| 4,732,154 | 3/1988 | Shiber . |
| 4,745,919 | 5/1988 | Bundy et al. . |
| 4,890,611 | 1/1990 | Monfort et al. . |
| 4,909,781 | 3/1990 | Husted . |
| 4,950,277 | 8/1990 | Farr . |
| 4,979,939 | 12/1990 | Shiber . |
| 5,007,896 | 4/1991 | Shiber . |
| 5,011,488 | 4/1991 | Ginsburg . |
| 5,030,201 | 7/1991 | Palestrant . |
| 5,047,040 | 9/1991 | Simpson et al. . |
| 5,052,404 | 10/1991 | Hodgson . |
| 5,054,501 | 10/1991 | Chuttani et al. . |

(List continued on next page.)

FOREIGN PATENT DOCUMENTS

| | | |
|---|---|---|
| 0448859 | 10/1991 | European Pat. Off. . |
| 0254414 | 8/1992 | European Pat. Off. . |
| 0501772 | 9/1992 | European Pat. Off. . |
| 0360791 | 8/1994 | European Pat. Off. . |
| 0337918 | 11/1994 | European Pat. Off. . |
| 0421457 | 1/1995 | European Pat. Off. . |
| 0379786 | 3/1995 | European Pat. Off. . |
| 0680730 | 11/1995 | European Pat. Off. . |
| 0442137 | 2/1996 | European Pat. Off. . |
| WO 82/04388 | 12/1982 | WIPO . |
| WO 89/00835 | 2/1989 | WIPO . |
| WO 94/04081 | 3/1994 | WIPO . |
| WO 94/10919 | 5/1994 | WIPO . |
| WO 95/27443 | 10/1995 | WIPO . |
| WO 96/39084 | 12/1996 | WIPO . |

*Primary Examiner*—Michael Buiz
*Assistant Examiner*—Kevin Truong
*Attorney, Agent, or Firm*—Townsend and Townsend and Crew LLP

[57] ABSTRACT

An apparatus and method of making a guidewire with a preformed three dimensional profile is described. The Apparatus comprises a mandrel having a screw thread for receiving a core wire and at least one securing means for holding the core wire onto the mandrel. The core wire must be retained under tension in order to properly impart the desired shape into the core wire. A system and method of using the apparatus is disclosed comprising the steps of loading the core wire onto the mandrel, securing the core wire and mandrel and then heating the assembly until the wire takes the desired shape.

15 Claims, 6 Drawing Sheets

U.S. PATENT DOCUMENTS

| | | |
|---|---|---|
| 5,078,722 | 1/1992 | Stevens . |
| 5,078,723 | 1/1992 | Dance et al. . |
| 5,100,423 | 3/1992 | Fearnot . |
| 5,103,543 | 4/1992 | Hodgson . |
| 5,116,352 | 5/1992 | Schnepp-Pesch et al. . |
| 5,135,531 | 8/1992 | Shiber . |
| 5,143,085 | 9/1992 | Wilson . |
| 5,158,564 | 10/1992 | Schnepp-Pesch et al. . |
| 5,195,954 | 3/1993 | Schnepp-Pesch et al. . |
| 5,224,945 | 7/1993 | Pannek, Jr. . |
| 5,251,640 | 10/1993 | Osborne . |
| 5,269,751 | 12/1993 | Kaliman et al. . |
| 5,306,244 | 4/1994 | Shiber . |
| 5,306,252 | 4/1994 | Yutori et al. . |
| 5,314,407 | 5/1994 | Auth et al. . |
| 5,314,438 | 5/1994 | Shturman . |
| 5,318,576 | 6/1994 | Plassche, Jr. et al. . |
| 5,320,634 | 6/1994 | Vigil et al. . |
| 5,334,211 | 8/1994 | Shiber . |
| 5,356,418 | 10/1994 | Shturman . |
| 5,360,432 | 11/1994 | Shturman . |
| 5,402,799 | 4/1995 | Colon et al. . |
| 5,403,334 | 4/1995 | Evans et al. . |
| 5,409,015 | 4/1995 | Palermo . |
| 5,417,703 | 5/1995 | Brown et al. . |
| 5,443,443 | 8/1995 | Shiber . |
| 5,488,958 | 2/1996 | Topel et al. ............................. 606/180 |
| 5,490,859 | 2/1996 | Mische et al. . |
| 5,501,694 | 3/1996 | Ressemann et al. . |
| 5,514,115 | 5/1996 | Frantzen et al. . |
| 5,522,875 | 6/1996 | Gates et al. . |
| 5,527,326 | 6/1996 | Hermann et al. . |
| 5,540,707 | 7/1996 | Ressemann et al. . |
| 5,556,408 | 9/1996 | Farhat . |
| 5,569,277 | 10/1996 | Evans et al. . |
| 5,571,122 | 11/1996 | Kelley et al. . |
| 5,584,843 | 12/1996 | Wulfman et al. . |
| 5,596,996 | 1/1997 | Johanson et al. . |
| 5,616,149 | 4/1997 | Barath ..................................... 606/159 |
| 5,620,451 | 4/1997 | Rosborough . |
| 5,622,188 | 4/1997 | Plaia et al. . |
| 5,643,298 | 7/1997 | Nordgren et al. . |
| 5,746,701 | 5/1998 | Noone ..................................... 600/585 |
| 5,876,414 | 3/1999 | Straub . |

APPARATUS FOR MAKING WIRE WITH RADIAL EXPANSIBLE GUIDE SECTION AND METHODS OF MANUFACTURING THE SAME

CROSS-REFERENCES TO RELATED APPLICATIONS

This application is a continuation-in-part of co-pending application Ser. No. 08/966,001, filed No. 7, 1997 now pending, and that application in its entirety is hereby incorporated by reference. In addition this application references and claims the benefit under 37 CFR §1.78 of provisional application Nos.60/081,631 filed Apr. 13, 1998; 60/103,447 filed Oct. 7, 1998; and 60/081,614, filed Apr. 13, 1998 the full disclosure of which are also incorporated herein by reference. The subject matter of this application is related to that of co-pending applications entitled "GUIDEWIRE FOR PRECISION CATHETER POSITIONING," and "VARIABLE STIFFNESS CATHETER FOR THE TREATMENT OF A BODY LUMEN, SYSTEMS AND METHODS FOR USING THE SAME," filed on the same date as the present application, the full disclosures of which are incorporated herein by reference.

BACKGROUND OF THE INVENTION

1. Field of the Invention

The present invention relates generally to an apparatus and method of making a guidewire with a preformed three dimensional profile for use in guiding a catheter or other medical device to a desired location within a body lumen.

2. Description of the Background Art

Medical guidewires are used primarily to facilitate the placement of catheters and endoscopic instruments within the tortuous paths of body conduits. For example, if it is desirable to place a catheter within the vascular system of a patient, a guidewire is first inserted into the vessel and then guided through the tortuous path desired for the catheter. Then the catheter is threaded over the guidewire. As the catheter is advanced it tends to follow the direction of the guidewire so that it ultimately negotiates the same tortuous path. Once the catheter is in its final operative position, the guidewire can be removed leaving the catheter to perform its desired function.

Guidewires are traditionally utilized to negotiate the complex vascular system of a patient to guide a medical device, (e.g. a catheter) to a desired location. It has been in the past of paramount importance for the guidewire to have a shape which provides for superior navigation a patient's vascular system. Inventions in the field include guidewires with floppy tips, improved methods of manufacturing, increased torquability and improved friction reducing features to help catheters move over the guidewires. Thus the focus of the prior art has been to create a guidewire with the ability to create a path along which a catheter could follow to reach a particular site of the body.

Guidewires often use transition areas of changing diameter along their length. A smooth transition gives the guidewire the ability to better negotiate tight bends in the anatomy of the patient. The transition area of a guidewire may be long or short, that is the change from one diameter along the length of the guidewire may occur over a few millimeters, or several centimeters. In the past the use of transition areas has been combined with the use of a filament wire which covers the narrower distal section of the guidewire. The combination, well understood in the art, provides the distal tip of the wire with a greater flexibility to steer through the vasculature of a patient, while the filament wire provides added strength and radiopacity. The filament wire can also be used as a fastening point for the attachment of an atraumatic tip. Examples of guidewires using the combination of transition areas and filament wires are described in Colon et al., (U.S. Pat. No. 5,402,799) and Ashby et al., (U.S. Pat. No. 5,622,184). Others have modified the basic design by using other materials, such as Johanson et al., (U.S. Pat. No. 5,596,996). However all of the prior art to date has used guidewires for essentially the same purpose, to navigate the anatomy of a patient and direct a catheter to a particular sight within a body lumen. The medical procedure to be carried out is then conducted by the catheter. There are specialized guidewires which have been developed which attempt to do the job of a catheter using a modified guidewire. Two examples are guidewires with imaging and non-imaging sensors.

However there remains a need for a guidewire which can steer a catheter more particularly to a precise position within the vascular system of the patient. More particularly it would be beneficial to be able to manufacture a guidewire able to direct a catheter to a particular side of a lumen in the event a physician wishes to treat one side of a body lumen and not another, or be able to direct a catheter to precise locations of a body lumen. Straight guidewires are unable to perform this feat, however a novel guidewire has been disclosed in co-pending application Ser. No. 08/966,001 which is capable of steering catheters to a particular side of a body lumen.

SUMMARY OF THE INVENTION

The present invention relates to an apparatus and method of manufacturing a medical guidewire having a preformed curved three dimensional profile as described in co-pending U.S. application Ser. No. 08/966,001.

The apparatus for making a guidewire having a preformed three dimensional profile comprises a mandrel having a temperature stable core and at least one screw thread along part of the mandrel's length. In addition the apparatus includes a restraining means for securing the wire to the mandrel so that tension in the wire is maintained during a heating step. The retaining device may be a screw, a friction lever or other means used to secure the wire in place when an operator wraps the wire over the mandrel. The mandrel has an inscribed helical channel which may be either regular or irregular in shape. The mandrel of the present invention acts as a negative die, and a core wire will assume the positive shape of the mandrel using the method described below.

A system is described for automating the construction of the shape setting process. The system comprises a rotatable chuck for holding the mandrel, and a spring tension arm for maintaining the tension of the core wire while the core wire is loaded onto the mandrel. The system also includes a heating element for providing the heat necessary for accomplishing the shape setting step of the method described below. The rotatable chuck may be turned by hand or mounted on a lathe. Furthermore the system may be automated by using a computer controller for handling the rotational speed of the chuck. Speed determination and the proper winding of the core wire around the mandrel could be handled by a sensor such as a roto-optical feedback unit.

A method of making the wire is disclosed which includes the steps of wrapping a core wire around a mandrel such that the wire winds fall into the spaced apart roots of the mandrel.

The wire must be secured tightly so the core wire is under tension while wound on the mandrel. The wire must be secured at both ends of the mandrel using a securing device like a clamp, screw or temporary bonding agent so the wire does not move or come loose during the shape setting step. The mandrel assembly is then heated to a temperature between 200 and 800 degrees centigrade. This is the shape setting step. The mandrel is left at the shape setting temperature as long as necessary for the core wire to take the desired shape set. The exact temperature and duration depend on the alloy used in the core wire. Some alloys require greater incubation times or temperatures than others in order to achieve a shape set result for a shape memory alloy. Once the shape setting step is completed the mandrel assembly is removed from the oven or heating area and allowed to cool to room temperature. The cooling may be either a quenching in water, or air cooling. Once the mandrel assembly has returned to room temperature, the core wire must be carefully unwound form the mandrel to protect the wire from damage.

The shaped core wire can be coated with a compound such as Teflon (PTFE) or some other bio-compatible material. A filament wire may be added as is common practice in the field of guidewire manufacturing. A greater understanding of the apparatus and methods can be had from a review of the following description.

DESCRIPTION OF THE SPECIFIC EMBODIMENTS

The following detailed descriptions are the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

While common guidewire terminology is used herein, clarification of certain terms is necessary. Terms used in the field of guidewire manufacturing and guidewire usage often vary among physicians and practitioners. The present invention is designed to take a straight core wire and reshape it into a form suitable for use in interventional procedures. The "Core Wire" is the back bone of a guidewire. Frequently made from a bio-compatible alloys such as stainless steel or nickel-titanium, these wires are usually larger at the proximal side and tapered to a thinner diameter at the distal end. The taper of the guidewire can be constant along the length, or broken up into transition areas as described above. Along the distal tip of the guidewire, a small coil is often slid over and secured to the core wire. The small wire which is used to make the coil is referred to herein as the "Filament wire". The diameter of a regular guidewire used in cardiology procedures is generally about 0.014". For purposes of discussion the core wires used in the present invention follow the same geometries of the core wires used in other guidewires.

A tapered core wire is used as the starting material for making a guidewire having a three dimensional profile. By "Three Dimensional Profile" we refer to the shape the wire assumes after it has gone through the procedure established below. Once the shape setting step is complete, the core wire can be modified as any other guidewire may be by techniques well understood in the art. While most guidewires are used to guide a catheter from a point of entry from outside a patients body to a desired location, the guidewire of the present invention is preferably utilized to direct a catheter to precise locations in a body lumen after the catheter has already been guided to the general site of interest using a standard guidewire. The present invention may be used for both introducing the catheter and for localized guidance if the guidewire is composed of a two way shape memory material.

Figure 1A:
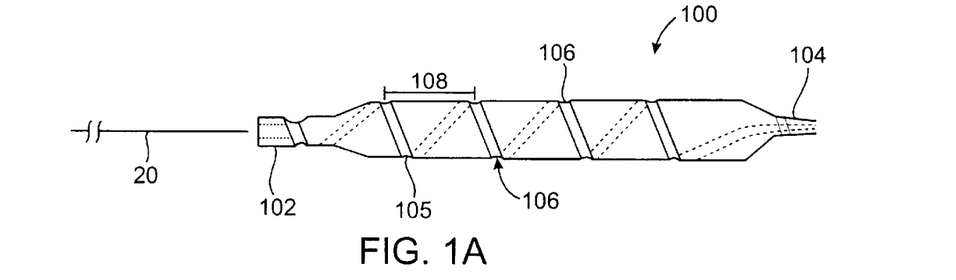
FIG. 1A shows a plan view of the mandrel.

FIG. 1A illustrates a plan view of a mandrel 100 in its basic form. The mandrel 100 has a proximal end 102 and a distal end 104 for reference. A helical screw thread 105 is engraved into the mandrel 100. The screw thread 105 has a defined pitch 108 used to establish the distance between the coils of the wire (see below) once the shape setting procedure is complete. The screw thread 105 has spaced apart roots 106 for receiving the core wire 20. It is important the mandrel 100 be made from a temperature stable material for the operation of making the shaped guidewire. The mandrel 100 may be made of brass, steel, ceramics or any other material which will retain its shape at temperatures up to 800 degrees Centigrade. The diameter of the mandrel between the bottom of the roots 106 is the minor diameter 128. The minor diameter 128 determines the minimum inner diameter of the core wire 20 after the shape setting is complete.

Figure 1B:
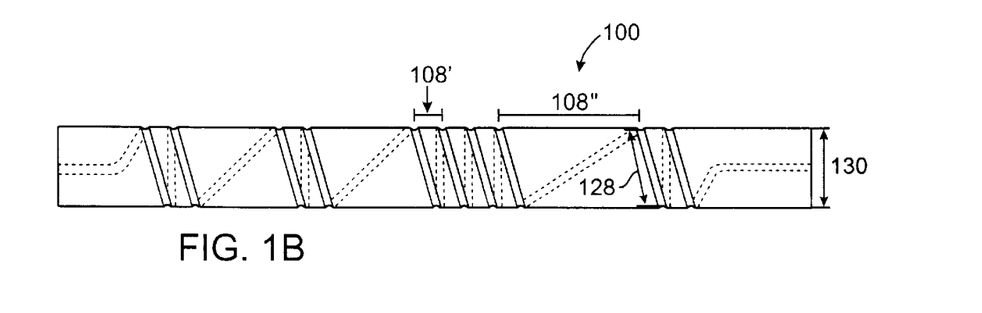
FIGS. 1B and 1C show alternative mandrel designs.
Figure 1C:
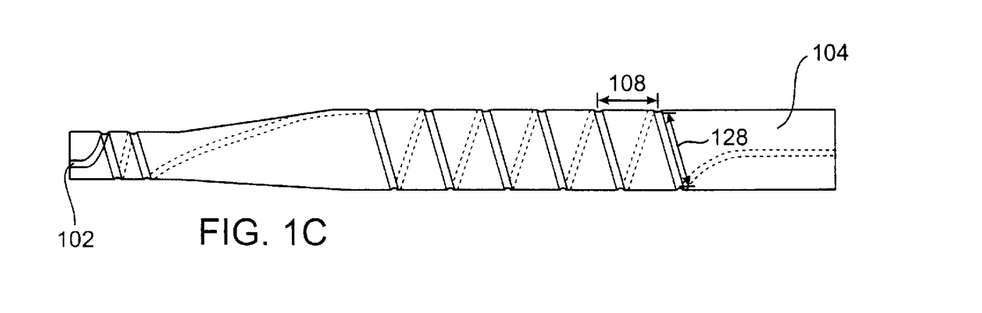

FIG. 1B shows a mandrel 100 that can be used to produce a guidewire where the pitch is uneven along the length of the three dimensional profile of the wire. FIG. 1C shows another mandrel 100 where the diameter of the wire's helical winds may be varied. FIG. 1D shows a mandrel having a square cross section normal to its main axis. The variation can produce a guidewire with a much more angular shape if desired. Because of the ability of shape memory alloys to assume a tremendous assortment of shapes, the mandrel 100 may be designed with any combination of cross section geometries and diameters. However it should be apparent that the smoother the outer perimeter of the wire during usage, the less traumatic the guidewire will be to the patient. Thus it is preferred to utilize a regularly curved helical structure when possible.

Figure 2A:
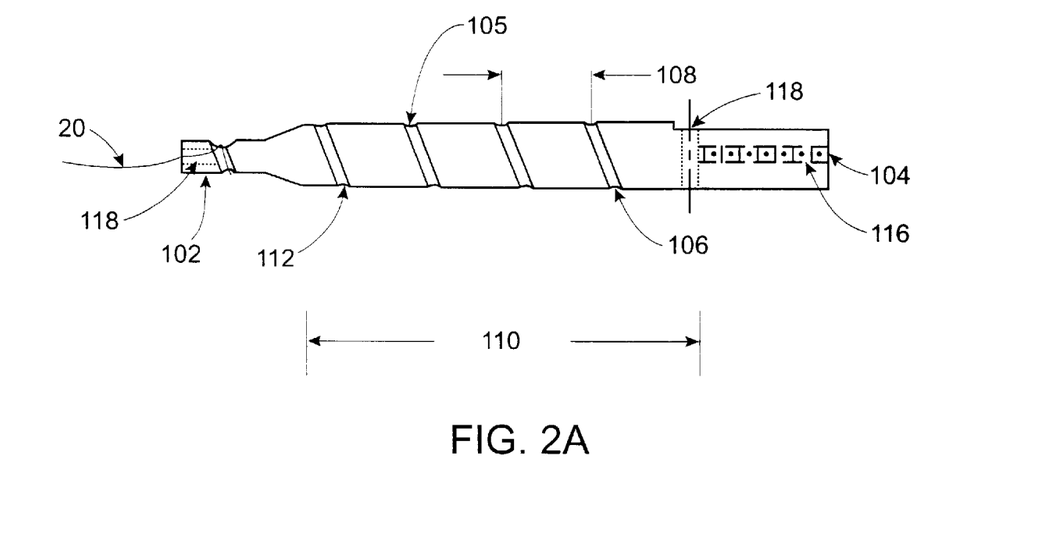
FIGS. 2A, 2C and 2D show three steps in the method of making the wire of the present invention.

FIGS. 2A–2F show a series of drawings where the method of the present invention is employed to produce a guidewire having a shaped three dimensional profile. The Mandrel 100 in FIG. 2A is shown with a core wire 20 being introduced into the proximal tip 102. The winding procedure may be done by hand. If done by hand, the operator feeds a predetermined length of the core wire 20 through the wire entry port 118 on the proximal tip 102. Once the appropriate amount is fed through the first wire entry port 118, the core wire 20 is secured at the proximal end 102. The core wire 20 is wound around the screw threads 105 either by a machine or an operator, and the core wire 20 is wound tightly so tension remains in the core wire 20 during the shape setting procedure. The operator must be careful to make sure each wind in the roots 106 is tight. If the wire is not tightly wound around the mandrel 100 during the shape setting step (see below) the wire will not retain the shape of the mandrel 100. Alternatively the operator may feed any length of the core wire 20 through the first wire entry port 118 and simply clip off any excess core wire 20 that remains after the winding procedure.

Figure 2B:
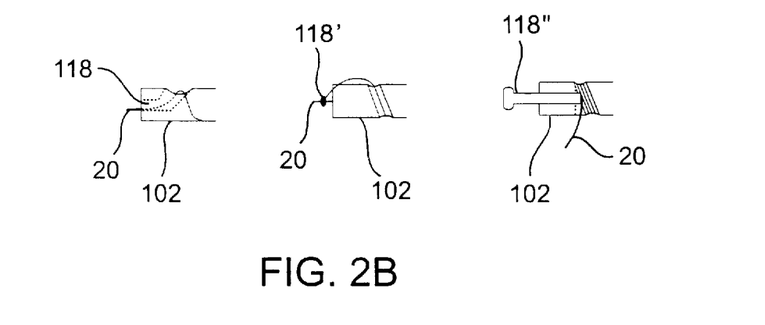
FIG. 2B shows three variations on the entry port design.

FIG. 2B shows the mandrel 100 with a variety of wire entry ports 118. The main consideration in the design of the wire entry port 118 is simply to be able to secure the core wire to the mandrel 100 without damaging the core wire 20. Thus the wire entry port 118 may be a simple channel, an eyelet 118', pin press 118" or any other receptacle capable of holding the wire in place.

Figure 2C:
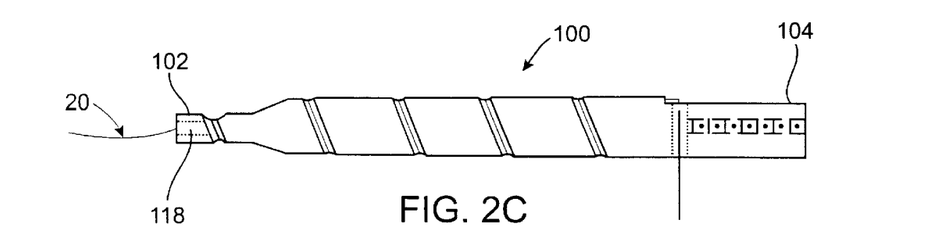
Figure 2D:
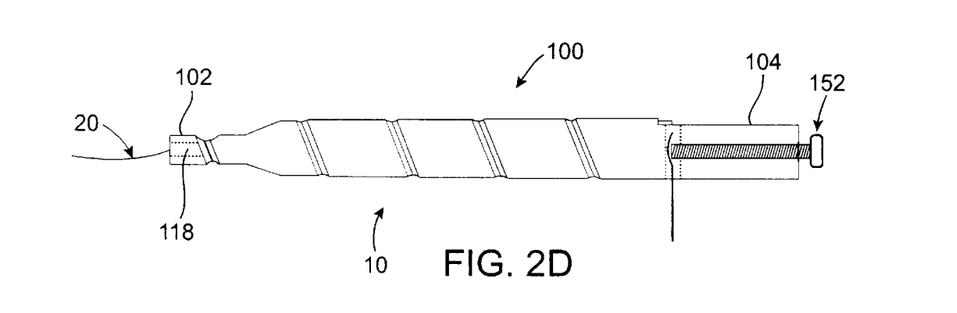

FIG. 2C shows the core wire 20 fully wrapped around the mandrel 100. The core wire 20 is fed through both wire entry ports 118 on the distal tip 102 and the distal end 104. Once the core wire 20 is fully wrapped around the mandrel 100, a second core wire securing means 152 (FIG. 2D) is used at the distal end 104 to make sure tension remains in the core wire 20 about the mandrel 100. The core wire 20 and mandrel 100 together comprise the mandrel assembly 10. The mandrel assembly 10 is then heated to the appropriate shape setting temperature which corresponds to that of the shape memory alloy being used. For Nickel and Titanium alloys, the temperature is preferably between 200 and 800 degrees Centigrade. In the case of two way shape memory alloys, the shape setting temperature should also be between 200 and 800 degrees centigrade while the transition temperature between austenite and martensite phases can be any temperature which is not the same as the heat set temperature.

Figure 2E:
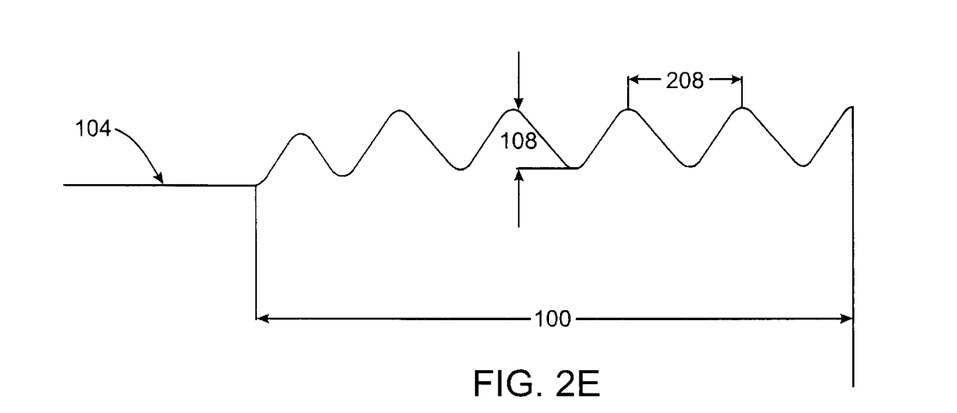
FIG. 2E shows a sample wire profile made using a mandrel of the present invention.

FIG. 2E shows the completed core wire 20 after the shape setting procedure. The core wire's pitch 208 corresponds closely to the pitch 108 of the mandrel 100. The general shape of the core wire 20 after the shape setting should be fairly close to that of the mandrel 100.

Figure 2F:
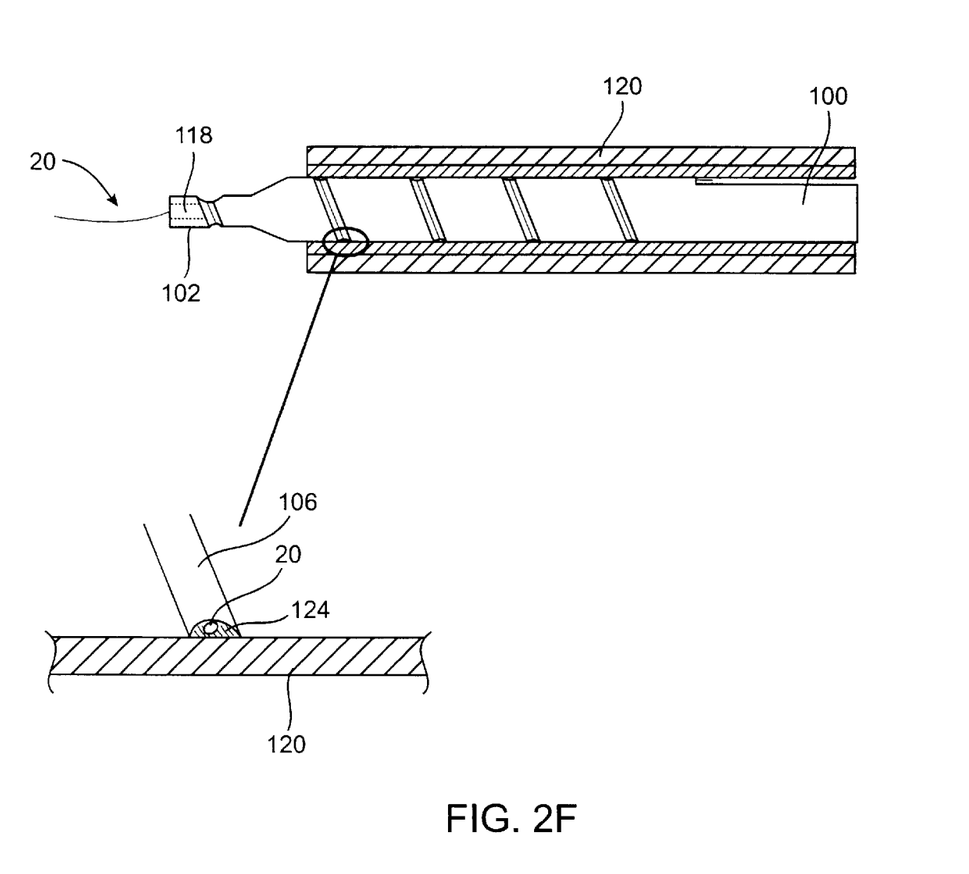
FIG. 2F shows an alternative mandrel assembly.

FIG. 2F shows another variation on the securing means used to provide the tension fit between the core wire 20 and the mandrel 100. A sleeve 120 with an inner diameter 122 frictionally engages the outer diameter of the mandrel 100 when the core wire 20 is wrapped around the mandrel 100. Using this embodiment it is necessary for the core wire 20 to be at least as high as the mandrel 100 outer surface so the core wire 20 can also frictionally engage the sleeve 122. Alternatively the sleeve 122 may have a heat stable cushion 124 so that the cushion 124 may fill the gaps 126 in between the root 106 and the core wire 20. Such a cushion may be any material well known in the art such as steel wool. The sleeve 122 may be a cylinder or a foldable device which can be wrapped around the mandrel assembly 10 and then itself secured in place. A blow up focusing on the interface between the mandrel 100 and the sleeve 122 is also shown.

Figure 3A:
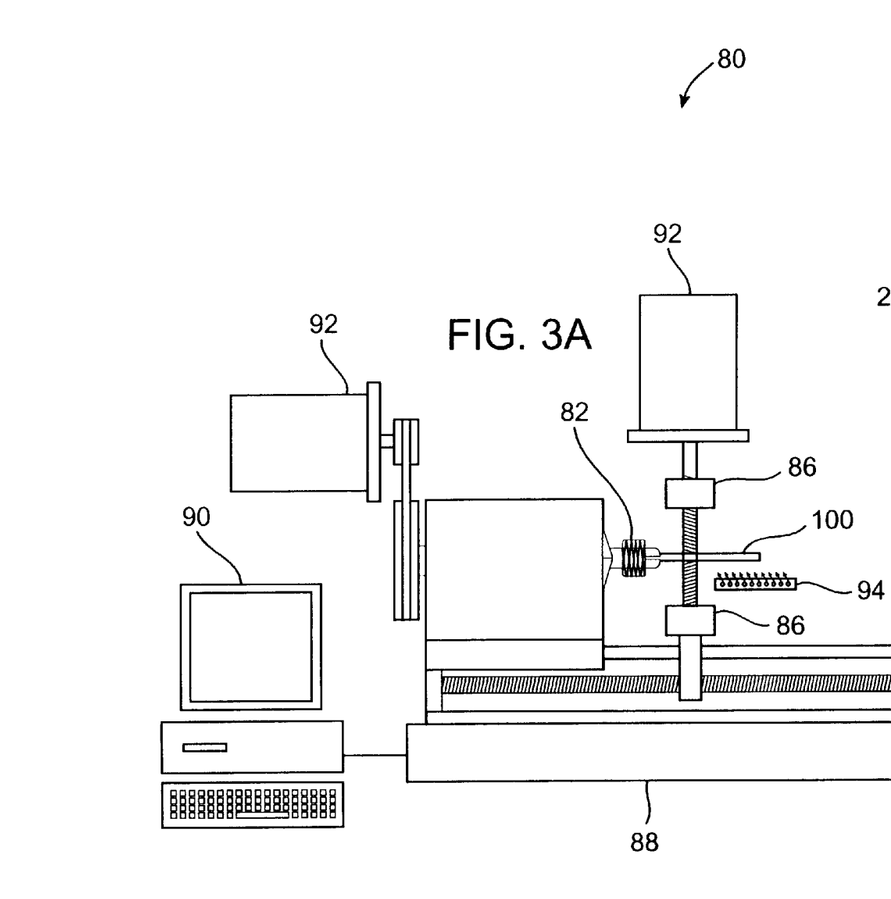
FIGS. 3A and 3B show a plan and side view of an automated device employing the present method.
Figure 3B:
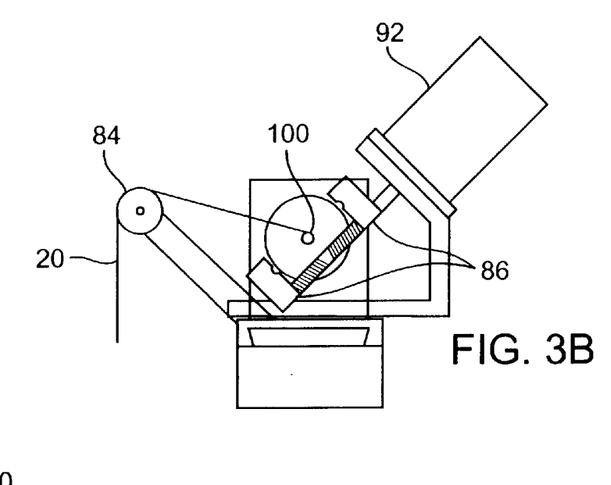

FIG. 3A shows a plan view of a system according to the present invention. The system 80 comprises a rotatable chuck 82 for holding the mandrel 100, and a spring tension arm 84 for maintaining the tension of the core wire 20 while the core wire 20 is loaded onto the mandrel 100. The system 80 also includes a heating element 86 for providing the heat necessary for accomplishing the shape setting step of the method described below. The rotatable chuck 82 may be turned by hand or mounted on a lathe 88. Furthermore the system 80 may be automated by using a computer controller 90 for handling the rotational speed of the chuck 82. Speed determination and the proper winding of the core wire 20 around the mandrel 100 is handled by a plurality of stepper motors 92. The heating element 86 need not be actual heaters, but can be any means known in the art to increase thermal temperatures, such as a salt bath, induction or RF system. An air cooling fan or blower 94 can be used to cool the mandrel 100 after the shape setting is finished. FIG. 3B shows an end view of the system described in FIG. 3A.

Figure 4A:
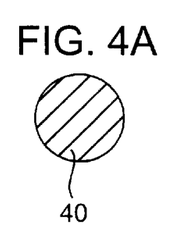
FIGS. 4A through 4F illustrate six possible cross sections of core wires that may be used in the present invention.
Figure 4B:
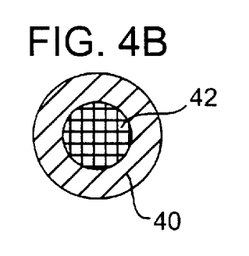
Figure 4C:
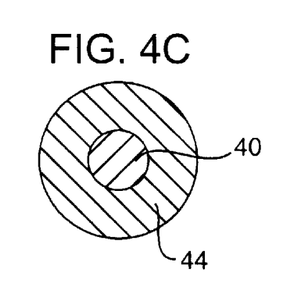
Figure 4D:
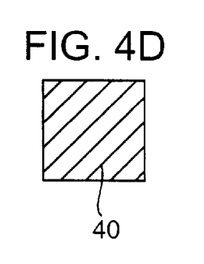
Figure 4E:
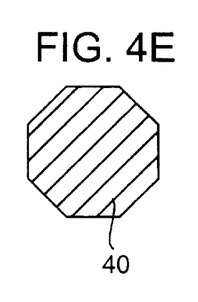
Figure 4F:
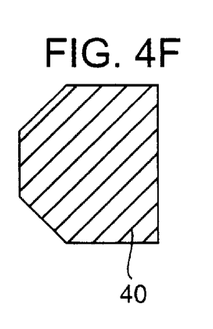

FIGS. 4A through 4F show alternative core wires 20 which may be used in the present invention. Any material that can be shape set at a particular temperature, and has a high degree of elastic or super elastic behavior may be used in the current invention. Aside from a core wire of a single material or single alloy (FIG. 4A), the core wire may represent a complex structure such as a shape memory alloy hypo-tube with a high density metal as the core (FIG. 4B). An example would be a gold core wire with a nickel-titanium hypo-tube, the combination then being co-axial, and then the two being shape set using the method described above. The advantage of using a core wire comprising a sandwich or tube arrangement is greater radiopacity or lateral strength may be imparted to the core wire, depending on the particular desire of the manufacturer. FIG. 4C shows a shape memory alloy 40 as the core element and a different material 44 as the cladding. FIGS. 4D–4F show three different cross sections for a shape memory alloy core wire 40.

What is claimed is:

1. An apparatus for shape setting a wire with a curved three dimensional guide section, said apparatus comprising:
    a mandrel having a temperature stable core, at least one screw thread having spaced apart roots capable of mechanically receiving a wire; and
    a means for retaining said wire under tension within said spaced apart roots and preventing said wire from slipping or shifting.

2. The apparatus of claim 1, wherein said mandrel has a minor diameter between 0.5 and 20 mm.

3. The apparatus of claim 1, wherein said mandrel has a non-uniform minor diameter.

4. The apparatus of claim 1, wherein said mandrel has a uniform linear geometry.

5. The apparatus of claim 1, wherein said mandrel has a non-uniform linear geometry.

6. The apparatus of claim 1, wherein the mandrel has a plurality of cross section geometries.

7. The apparatus of claim 1, wherein said cross sectional geometries are any combination of regular and irregular shapes.

8. The apparatus of claim 1, wherein the distance between said roots is between 0.026 mm and 12.7 mm.

9. The apparatus of claim 1, wherein the distance between said roots is preferably between 1 mm and 6 mm.

10. The apparatus of claim 1, wherein said mandrel is hollow.

11. The apparatus of claim 1, wherein said mandrel is made of brass.

12. The apparatus of claim 1, wherein said mandrel is made of any form of steel.

13. The apparatus of claim 1, wherein said mandrel is made of a ceramic material.

14. The apparatus of claim 1, wherein said means is at least one clip.

15. The apparatus of claim 1, wherein said means is a tube slidably fit over said mandrel.

* * * * *